United States Patent
Golds

(10) Patent No.: US 6,881,221 B2
(45) Date of Patent: *Apr. 19, 2005

(54) TUBULAR STRUCTURE/STENT/STENT SECUREMENT MEMBER

(75) Inventor: Ellen Golds, Hastings-on-Hudson, NY (US)

(73) Assignee: SciMed Life Systems, Inc., Maple Grove, MN (US)

( * ) Notice: Subject to any disclaimer, the term of this patent is extended or adjusted under 35 U.S.C. 154(b) by 234 days.

This patent is subject to a terminal disclaimer.

(21) Appl. No.: 09/966,832

(22) Filed: Sep. 28, 2001

(65) Prior Publication Data

US 2002/0016627 A1 Feb. 7, 2002

Related U.S. Application Data

(63) Continuation of application No. 09/487,943, filed on Jan. 19, 2000, now Pat. No. 6,312,458.

(51) Int. Cl.$^7$ .................................................. A61F 2/06
(52) U.S. Cl. ...................................... 623/1.13; 623/1.33
(58) Field of Search ................................ 623/1.1, 1.13, 623/1.33

(56) References Cited

U.S. PATENT DOCUMENTS

| | | | |
|---|---|---|---|
| RE31,618 E | * | 7/1984 | Mano et al. .................. 623/1.1 |
| 5,019,090 A | | 5/1991 | Pinchuk |
| 5,104,404 A | | 4/1992 | Wolff |
| 5,133,732 A | | 7/1992 | Wiktor |
| 5,135,536 A | | 8/1992 | Hillstead |
| 5,171,262 A | | 12/1992 | MacGregor |
| 5,282,824 A | | 2/1994 | Gianturco |
| 5,405,377 A | | 4/1995 | Cragg |
| 5,476,508 A | | 12/1995 | Amstrup |
| 5,507,767 A | | 4/1996 | Maeda et al. |
| 5,507,768 A | | 4/1996 | Lau et al. |
| 5,507,771 A | | 4/1996 | Gianturco |
| 5,549,663 A | | 8/1996 | Cottone, Jr. |
| 5,554,183 A | | 9/1996 | Nazari |
| 5,556,426 A | * | 9/1996 | Popadiuk et al. ............ 623/1.1 |
| 5,575,816 A | | 11/1996 | Rudnick et al. |
| 5,607,478 A | | 3/1997 | Lentz et al. |
| 5,628,783 A | | 5/1997 | Quiachon et al. |
| 5,665,115 A | | 9/1997 | Cragg |
| 5,683,448 A | | 11/1997 | Cragg |
| 5,707,388 A | | 1/1998 | Lauterjung |
| 5,716,396 A | | 2/1998 | Williams, Jr. |
| 5,718,724 A | | 2/1998 | Goicoechea et al. |
| 5,976,192 A | * | 11/1999 | McIntyre et al. ............ 623/1.1 |
| 6,042,605 A | * | 3/2000 | Martin et al. ................. 623/1.1 |
| 6,312,458 B1 | * | 11/2001 | Golds ......................... 623/1.13 |

FOREIGN PATENT DOCUMENTS

| | | |
|---|---|---|
| WO | WO 95/26695 | 10/1995 |
| WO | WO 96/21404 | 7/1996 |
| WO | WO 96/21402 | 6/1997 |
| WO | WO 97/21403 | 6/1997 |
| WO | WO 97/33532 | 9/1997 |
| WO | WO 98/27894 | 7/1998 |

* cited by examiner

Primary Examiner—Julian W. Woo
(74) Attorney, Agent, or Firm—Hoffmann & Baron, LLP

(57) ABSTRACT

An improved endoluminal prosthesis is described which possesses increased flexibility and longitudinal compliance with a stent/graft/stent securement member combination.

9 Claims, 8 Drawing Sheets

TUBULAR STRUCTURE/STENT/STENT SECUREMENT MEMBER

This application is a continuation of application Ser. No. 09/487,943, filed on Jan. 19, 2000, now U.S. Pat. No. 6,312,458.

FIELD OF THE INVENTION

The present invention relates to an implantable endoluminal prosthesis. More particularly, the present invention relates to a stent-graft endoluminal prosthesis offering increased flexibility and compliance.

BACKGROUND OF THE INVENTION

An endoluminal prosthesis is a medical device commonly known to be used in the treatment of diseased blood vessels. An endoluminal prosthesis is typically used to repair, replace, or otherwise correct a damaged blood vessel. An artery or vein may be diseased in a variety of ways. An endoluminal prosthesis is therefore designed to be used to prevent or treat a wide variety of defects such as stenosis of the vessel, thrombosis, occlusion, or an aneurysm.

One type of endoluminal prosthesis used in the repair of diseases in various body vessels is a stent. A stent is a generally longitudinal tubular device formed of biocompatible material which is useful to open and support various lumens in the body. For example, stents may be used in the vascular system, urogenital tract and bile duct, as well as in a variety of other applications in the body. Endovascular stents have become widely used for the treatment of stenosis, strictures, and aneurysms in various blood vessels. These devices are implanted within the vessel to open and/or reinforce collapsing or partially occluded sections of the vessel.

Stents are generally open ended and are radially expandable between a generally unexpanded insertion diameter and an expanded implantation diameter which is greater than the unexpanded insertion diameter. Stents are often flexible in configuration, which allows them to be inserted through and conform to tortuous pathways in the blood vessel. The stent is generally inserted in a radially compressed state and expanded either through a self-expanding mechanism, or through the use of balloon catheters.

A graft is another type of endoluminal prosthesis which is used to repair and replace body vessels. Whereas a stent provides structural support to hold a damaged vessel open, a graft provides an artificial lumen through which blood may flow. Grafts are tubular devices which may be formed of a variety of materials, including textile and non-textile materials. One type of non-textile material particularly suitable for use as an implantable prosthesis is polytetrafluoroethylene (PTFE). PTFE exhibits superior biocompatibility and low thrombogenicity, which makes it particularly useful as vascular graft material in the repair or replacement of blood vessels. In vascular applications, the grafts are manufactured from expanded PTFE (ePTFE) tubes. These tubes have a microporous structure which allows natural tissue ingrowth and cell endothelialization once implanted in the vascular system. This contributes to long term healing and patency of the graft.

It is also known to combine a stent and a graft to form a composite medical device. Such a composite medical device provides additional support for blood flow through weakened sections of a blood vessel. In endovascular applications the use of a stent/graft combination is becoming increasingly important because the combination not only effectively allows the passage of blood therethrough, but also ensures the implant will remain open.

Several types of stent/graft inventions are known in the art. U.S. Pat. No. 5,151,105 issued to Kwan-Gett discloses a collapsible textile vessel sleeve with stent members positioned at opposite ends of the sleeve. The device is specifically designed to provide a vessel sleeve that is collapsible to a very small diameter in order that it may be placed in position within the abdominal or thoracic aorta by a catheter via the lumen of the femoral artery. Such a procedure obviates the need for a major surgical intervention, and reduces the risks associated with such a procedure.

Other stent/graft composite devices using a textile fabric are shown in U.S. Pat. No. 5,628,788 to Pinchuck.

As mentioned above, ePTFE may also be used as graft material in stent/graft endoprostheses. One example of an ePTFE stent/graft device is shown in U.S. Pat. No. 5,700,285 issued to Myers, et al. Myers discloses a tubular intraluminal graft in the form of a tubular diametrically adjustable stent having an interior and exterior tubular covering of porous expanded polytetrafluoroethylene. The tubular covering surrounds the stent so that the stent is contained during contraction and expansion in the delivery process.

Stents are effectively used in combination with grafts as the composite endoluminal prosthesis allows blood flow through the vessel created by the graft, while the stent maintains its patency. It has been found however that stent/graft composite devices exhibit reduced flexibility and longitudinal compliance. Longitudinal compliance is of particular importance to such stent/graft endoluminal prosthesis as the device must be intraluminally delivered through tortuous pathways of a blood vessel to the implantation site where the stent is expanded. The increased width creates a profile of increased size of the prosthesis which may present problems in placing and expanding the prosthesis in smaller arteries and veins which demand a smaller, more flexible endoluminal prosthesis. Such reduction of compliance and flexibility is caused by the increased thickness of the composite device and also by the technique used to secure the stent to the graft.

In order to solve such problems, several stent/graft devices have been developed. International publication number WO 97/21403 to Prograft discloses a stent graft combination comprising a stent member with an inner and outer surface, a tubular graft member, and a ribbon covering only a portion of at least one of the inner and outer surfaces of said stent member for securing the stent member and graft member to one another. This device uses a broad ribbon in order to increase the potential bonding surface area between the coupling member and the graft member to enhance the structural integrity of the stent/graft device while reducing the total thickness of the composite graft. The coupling ribbon used in the Prograft stent/graft device essentially tracks the path of the stent in coupling the stent to the graft, i.e., the coupling ribbon and the stent are helically wound to form a spiral configuration where both have the same angular orientation with respect to the longitudinal axis of the graft.

The use of such a broad coupling member, however, may present a variety of problems. The use of such a broad coupling member also may decrease the overall flexibility of the prosthesis. The use of a broad coupling member may furthermore, increase radial stiffness of the prosthesis. In addition wrapping the ribbon about the stent at the same angular orientation as the stent tends to decrease the flexibility and expandability of the stent.

It is desirable to provide a stent/graft composite device which secures the stent to the graft without exhibiting a significant reduction in longitudinal compliance or flexibility.

SUMMARY OF THE INVENTION

It is an advantage of the present invention to provide an endoluminal prosthesis including a stent/graft composite device having increased flexibility.

It is also an advantage of the present invention to provide a stent/graft composite device where the stent is secured to the graft so as to not reduce the flexibility and longitudinal compliance of the device.

The present invention provides a thin suture, or filament-like securement member which secures the stent to the graft by being helically arranged at an angle with respect to the longitudinal axis of the graft, such that the angle does not equal the angle formed with respect to the helical windings of the stent. The present invention is designed to be able to provide structural integrity for the prosthesis while also substantially reducing its size. The prosthesis exhibits a reduced profile and increased flexibility over prior art. Furthermore, by angularly orienting the wrap with respect to the stent, the radial wrap provides the prosthesis with a more efficient means of securing the stent cohesively together. The angular orientation in regard to the stent, further provides a more efficient means of securing the stent to the tubular member.

In attaining these and other advantages, the present invention provides an endoluminal prosthesis comprising a polytetrafluoroethylene tubular member with a luminal surface, an exterior surface, and a longitudinal axis. A diametrically deformable stent is circumferentially disposed on the luminal or exterior surface of said tubular member, said stent being formed from an elongate wire helically wound defining a plurality of spaced apart windings disposed at a first angle with respect to said longitudinal axis, and an elongate securement member securing said stent to said tubular member, said securement member being helically arranged at a second angle with respect to said longitudinal axis so that said first angle is not congruent to said second angle.

A method of making the endoluminal prosthesis of the present invention is also disclosed. The method comprises providing a polytetrafluoroethylene tubular member, said tubular member comprising a luminal surface, an exterior surface, and a longitudinal axis. The method of making the prosthesis further comprises disposing a diametrically deformable stent circumferentially on the luminal or exterior surface of said tubular member, said stent being formed from an elongate wire helically wound defining a plurality of spaced apart windings disposed at a first angle with respect to said longitudinal axis; and helically wrapping an elongate securement member to secure said stent to said tubular member, said elongate securement member being wrapped at a second angle with respect to said longitudinal axis, so that said second angle is not congruent to said first angle of said stent.

DETAILED DESCRIPTION OF THE INVENTION

The following is a detailed description of the preferred embodiments of the present invention. The description is meant to describe preferred embodiments, and is not meant to limit the invention in any way.

The present invention provides an improved endoluminal prosthesis comprising a polytetrafluoroethylene tubular member with a luminal surface, an exterior surface, and a longitudinal axis. A diametrically deformable stent is circumferentially disposed on the surface of the tubular member. The stent is formed from an elongate wire helically wound defining a plurality of spaced apart windings disposed at a first angle with respect to said longitudinal axis. An elongate securement member secures the stent to said tubular member, the securement member is helically arranged at a second angle with respect to said longitudinal axis so that said first angle is not congruent to said second angle.

The design allows securement of a stent to a graft in such a manner to ensure optimal properties of flexibility and reduced profile. Specifically, the helical angularly oriented direction of the securement member, which is wrapped circumferentially around the tubular member creates an angle with respect to the longitudinal axis of the tubular member which is incongruous to the angle at which the windings of the stent are disposed with respect to the longitudinal axis of the prosthesis. This allows for structural integrity of the prosthesis with a minimal amount of material comprising the securement member.

Various stent types and stent constructions may be employed in the present invention. Among the various stents useful include, without limitation, self-expanding stents and balloon expandable stents. The stents may be capable of radially contracting, as well, and in this sense can best be described as radially distensible or deformable. Self-expanding stents include those that have a spring-like action which causes the stent to radially expand, or stents which expand due to the memory properties of the stent material for a particular configuration at a certain temperature. Nitinol is one material which has the ability to perform well while both in spring-like mode, as well as in a memory mode based on temperature. Other materials are of course contemplated, such as stainless steel, platinum, gold, titanium, and other biocompatible metals, as well as polymeric stents.

Figure 1:
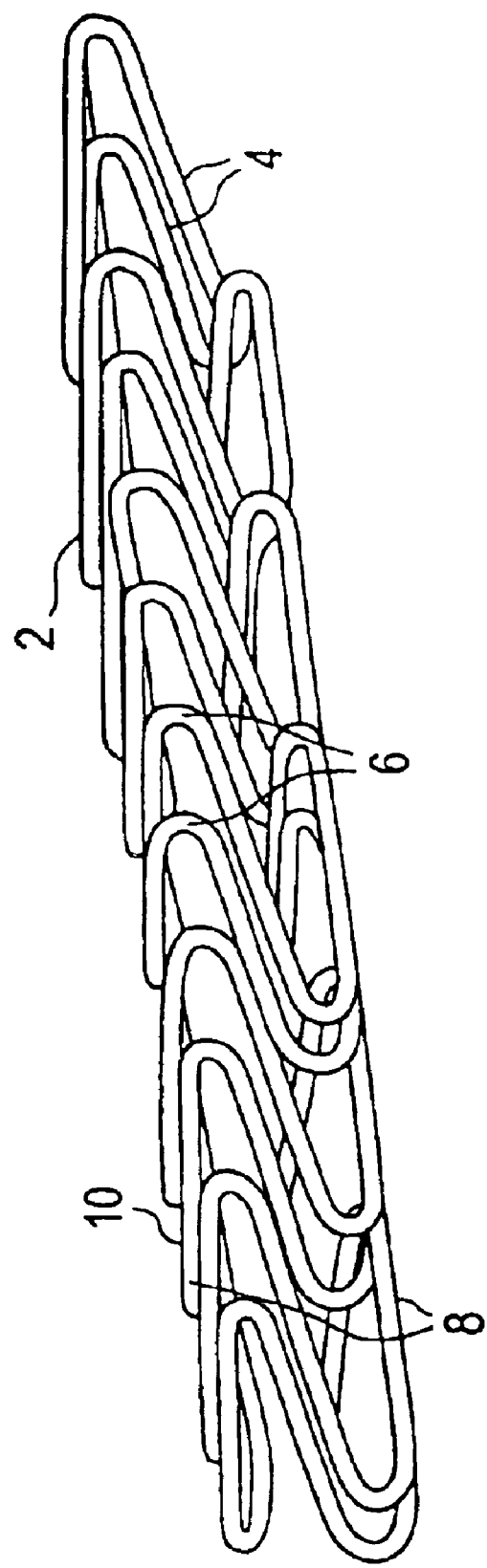
FIG. 1 is a perspective showing a collapsed wave-like stent which may be used in the present intraluminal prosthesis.
Figure 2:
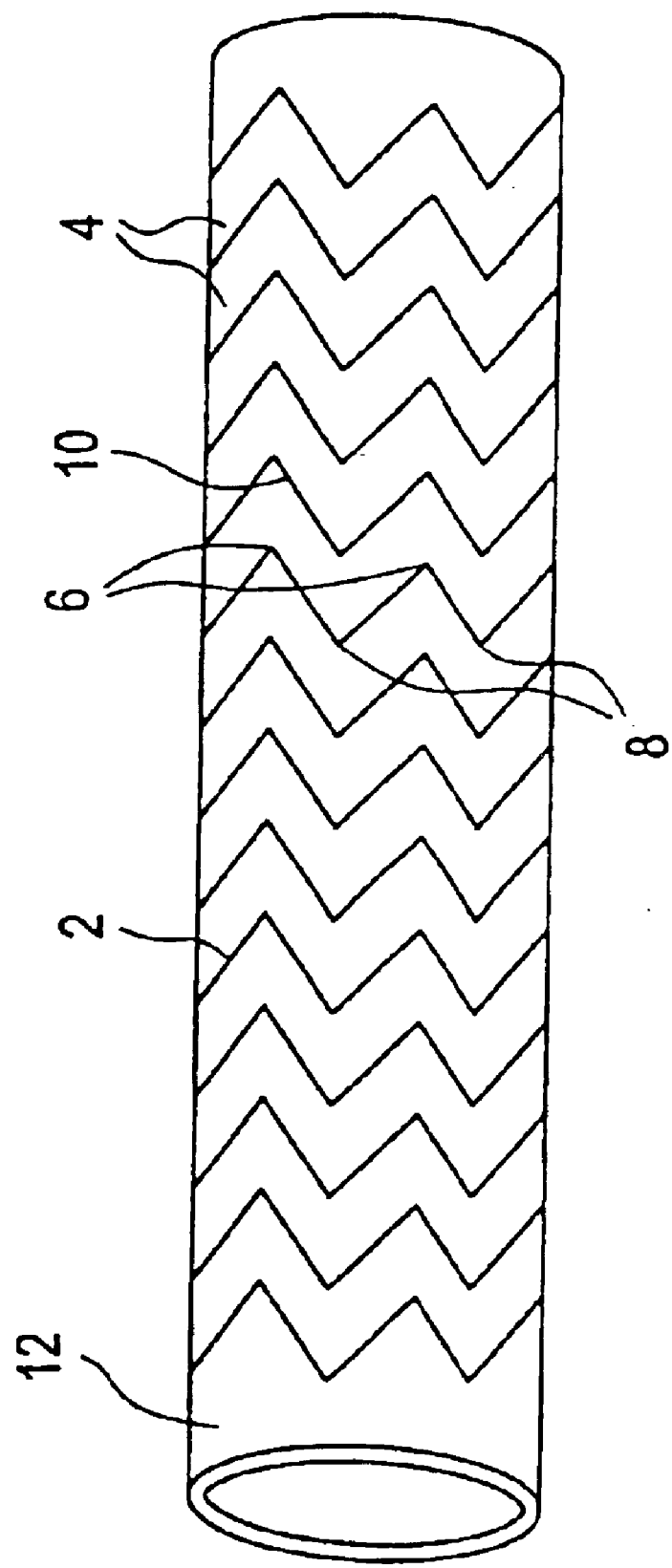
FIG. 2 is a perspective showing a stent similar to the stent of FIG. 1 expanded about an exterior surface of an ePTFE graft tube.

Referring now to FIGS. 1 and 2 of the drawings, the composite prosthesis 5 of the present invention includes a stent 2 shown in FIG. 1, as well as a similar stent 3 shown in FIG. 2 of the drawings. Stent 2 is shown in a collapsed configuration in FIG. 1. Stents 2 and 3 include a plurality of spaced apart windings 4 which include successive upper wave-like peaks 6 and lower wave-like peaks 8. The upper and lower wave-like peaks are connected via leg segments 10 of the stent. As seen in FIG. 2, stent 3 shows parallel windings 4 arranged along the longitudinal axis of the prosthesis in such a manner that upper wave-like peaks 6 are nested within lower wave-like peaks 8 of adjacent windings along the stent. As used in this disclosure, the term nested refers to the stent configuration where successive upper wave-like peaks of the stent are linearly aligned to fit within the successive lower wave-like peaks of the stent so that each wave is stacked (or nested) within the next adjacent winding. The stent shown in FIG. 1 is more fully described in commonly assigned U.S. Pat. No. 5,906,639 to Rudnick, et al., herein incorporated by reference.

Referring to FIG. 2 of the drawings, the tubular graft member 12 of the endoluminal prosthesis is preferably formed of polytetrafluoroethylene (PTFE). In vascular applications, prostheses are most often manufactured from expanded PTFE (ePTFE) tubes. As a result of the stretching and expansion of the PTFE material, these tubes have a microporous structure which allows natural tissue ingrowth and cell endothelialization once implanted in the vascular system. This contributes to long term healing and patency of the prosthesis. Tubular member 12 may be extruded as a tube or may be formed from an extruded sheet which is subsequently formed into a tubular structure. Textile or fabric constructions formed of PTFE or ePTFE yarns, filaments, or mesh may also be employed.

As shown in FIG. 2, stent 3 is applied in a radially expanded condition about the exterior surface of tubular graft member 12 to form a stent/graft composite of the type well known in the art. While the preferred embodiments described herein show stent 2 supported about the exterior surface of tubular graft member 12, it is within the contemplation of the present invention to support the stent on the opposed luminal surface thereof.

Figure 3:
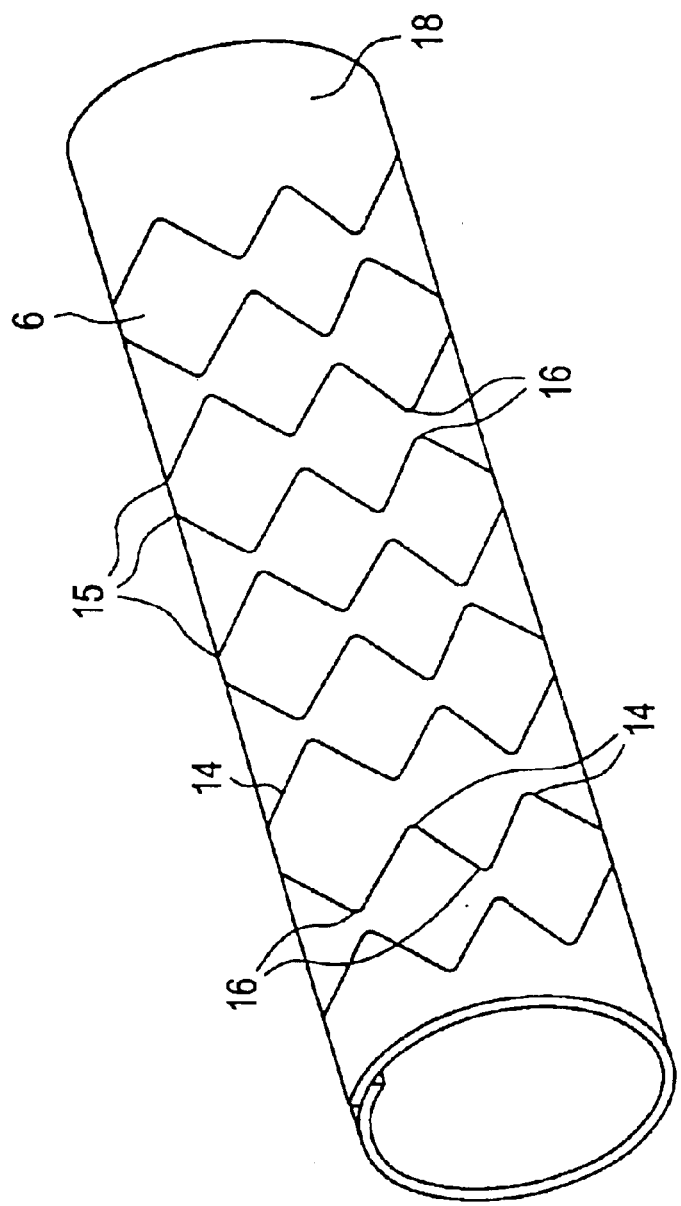
FIG. 3 is a perspective showing a composite endoluminal prosthesis comprising another stent embodiment disposed on the exterior surface of a tubular member.
Figure 4:
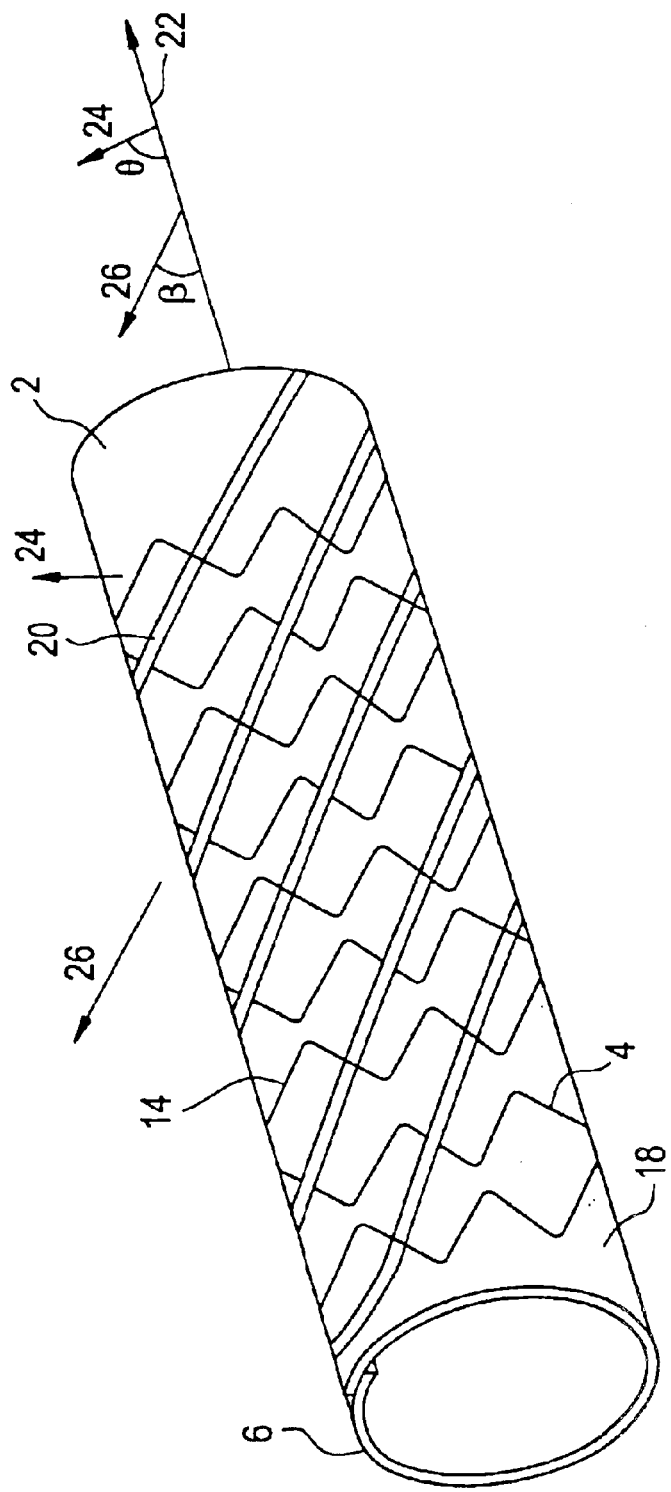
FIG. 4 is a perspective showing of the endoluminal prosthesis of FIG. 3 including a securement member for supporting the stent to the graft.

Referring now to FIGS. 3 and 4, a composite stent/graft device 17 is shown. Device 17 includes a stent 14 positioned about an ePTFE tube 18. In the present example tube 18 is formed from a sheet of ePTFE. Stent 14 is similarly formed of spaced apart windings comprising successive upper wave-like peaks and lower wave-like peaks connected via leg segments of the stent. As can be seen in FIG. 3, the upper wave-like peaks meet lower wave-like peaks of successive windings to form elbows of coincidence 16.

As mentioned above, diametrically deformable stent 14 is helically wound to define a plurality of spaced apart windings 15. Windings 15 are disposed at a first angle with respect to the longitudinal axis of the ePTFE tubular member. The longitudinal axis of tubular member 18 is shown with directional arrow 22. Successive windings 15 of stent 14 are positioned at a first angle (as shown with directional arrow 24) θ with respect to the longitudinal axis of tubular member 18.

The present invention provides a securement member 20 which is most preferably a flat, thin suture. Tape, thread, ribbon, or other elongate members may also be used. The securement member may be formed of a variety of materials. Securement member 20 is preferably less than 0.60 mm wide. The securement member is preferably made from a textile material. In using the term textile material in this disclosure, it is meant to indicate any material which may be used to combine with other pieces of the same material to become part of a larger piece of fabric. Some materials which may be used as the securement member include, but are not limited to PTFE, ePTFE, Polyethylene terephthalate (PET), Polyether ether ketone (PEEK), polypropylene, fluorinated ethylene propylene (FEP), nylon (polyamide), polyurethane (PU) and polyimide (PI), polybutylene terephthalate (PBT), polyurethane rubber (PUR), silicone and silicone rubber, and bio-absorbable materials, including poly (glycolic acid) (PGA), poly(lactic acid) (PLA).

As shown in FIG. 4 of the drawings, securement member 20 is helically arranged at a second angle β which is non-congruent to said first angle θ. This design construction allows the prosthesis to be thin-walled, compliant, and more flexible, because it provides structural integrity using less covering in the form of securement member 20. When securement member 20 is angled at a different angle (as compared to angle θ between the stent windings and axis) to longitudinal axis 22, it allows the securement of the stent to the graft using less material than previously used in prostheses of this type. More specifically, the angular arrangement of the securement member allows a thin securement member, which allows for a more flexible, and thinner composite prosthesis. Both angle θ and angle β may equal any value from 0° to 180° with respect to longitudinal axis 22.

As mentioned above, a stent is preferably mounted on the exterior surface of tubular member 18. Securement member 20 is then helically wrapped around tubular member 18 at angle β with respect to longitudinal axis 22 of tubular member 18. Securement member 20 may be wrapped completely exteriorly of stent 4, or it may be interwoven between stent 4 and the exterior surface of tubular member 18. Securement member 20 is then adhered to tubular member 18. Adherence is typically accomplished by sintering the composite prosthesis. Sintering, as used in the present disclosure means heating the composite prosthesis to a temperature below its melting point, yet sufficient to thermally adhere the prosthesis. The heat of sintering differs for different materials. An adhesive may be used with the sintering process or the securement member may be adhered with an adhesive without sintering.

The securement member 20 ensures the integrity of the composite prosthesis. The securement member is typically adhered to the tubular member in some manner, and may weave in and out of the leg segments of the stent in order to securely attach the stent. The term adhered as used in this disclosure refers to the attaching of the securement member to the tubular member in any manner. It includes without limitation, lamination, thermally adhering, sintering, RF welding, attaching with an adhesive, and any combination of the above. The securement member may be adhered non-continuously at selected areas, or may be continuously adhered throughout its entire length.

Figure 5:
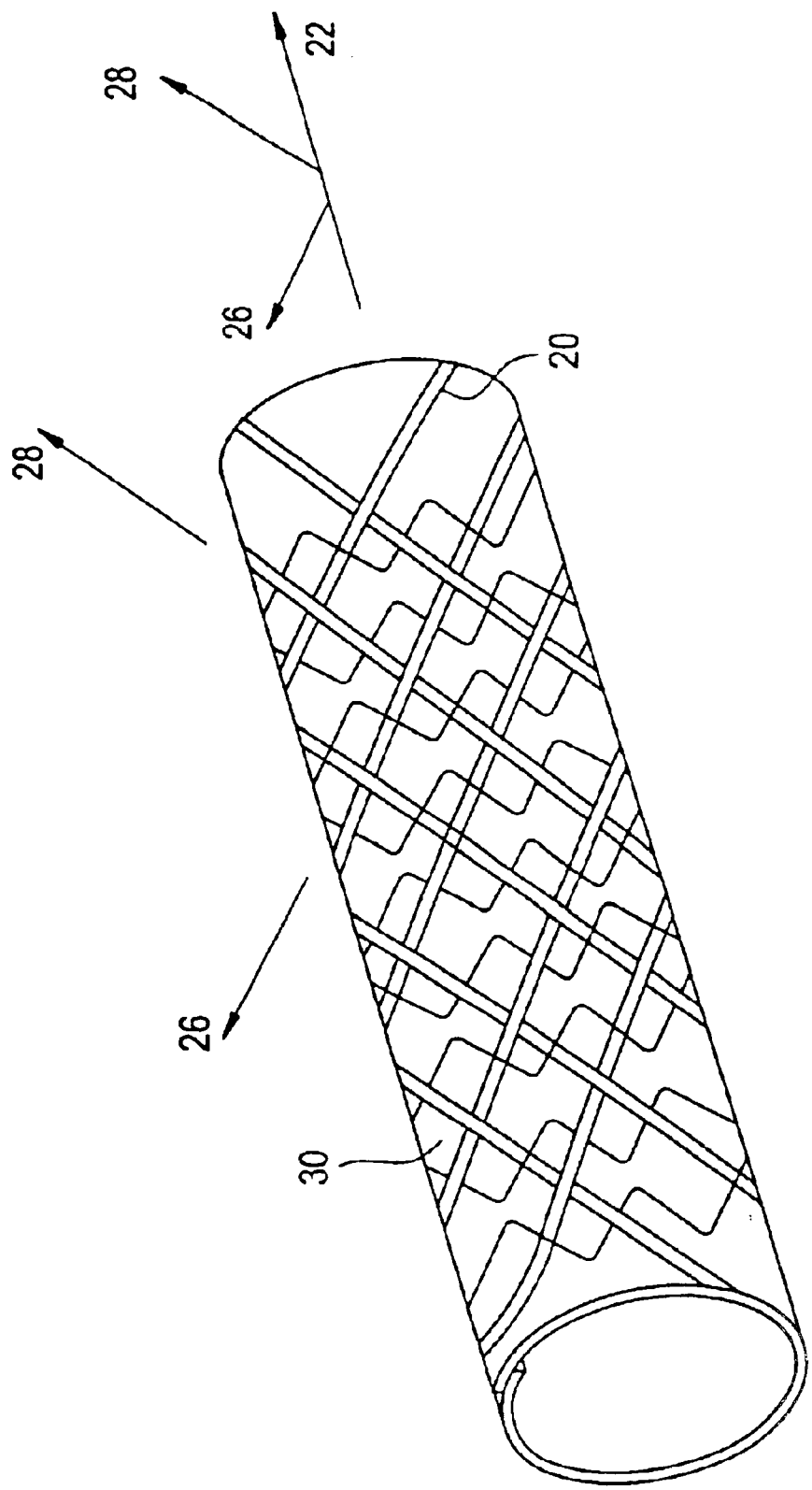
FIG. 5 is a perspective showing a further embodiment of the present invention with the securement member angularly oriented at two different angles to secure the stent to the tubular member.

Referring now to FIG. 5 of the drawings, securement member 20 may be wound at more than one angle with respect to the longitudinal axis 22. Directional arrows 26 and 28 show the different orientation (as well as the different angles they make as compared to the longitudinal axis 22) of the securement member with respect to longitudinal axis 22. When the securement member is orientated in two different directions with respect to the longitudinal axis as shown in FIG. 5, the securement member may intersect other helically oriented strips of the securement member to form nodes of intersection 30. Securement member 20 may be adhered to itself at nodes 30, or may be adhered to itself, as well as the tubular member. Preferably securement member 20 is sintered to itself at the segment it intersects, as well as to the tubular prosthesis at node 30.

Figure 6:
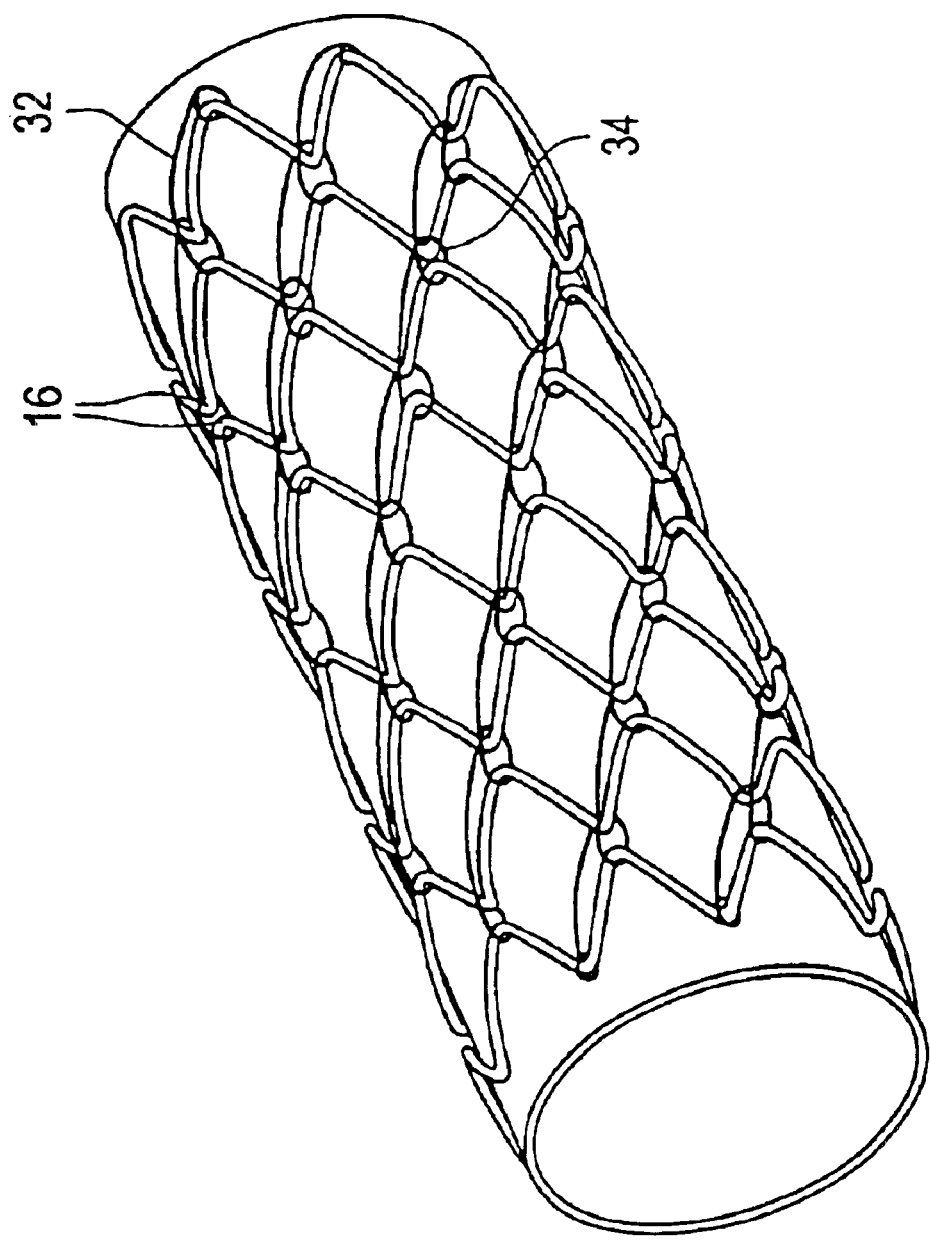
FIG. 6 is a perspective showing of a still further embodiment of an endoluminal prosthesis of the present invention wherein the securement member forms loops around elbows of the stent.

FIG. 6 shows another embodiment of the prosthesis of the present invention. Similar to the stent in FIG. 3, elbows of coincidence 16 are formed where the successive upper and lower wave-like peaks meet in successive stent windings. Thin suture 32 forms a loop around the peaks at the elbows of coincidence. In this manner, suture 32 forms eyelets 34 holding the successive peaks together at elbows 16. Suture 32 may be adhered to the tubular member at eyelets 34, preferably by lamination.

Figure 7:
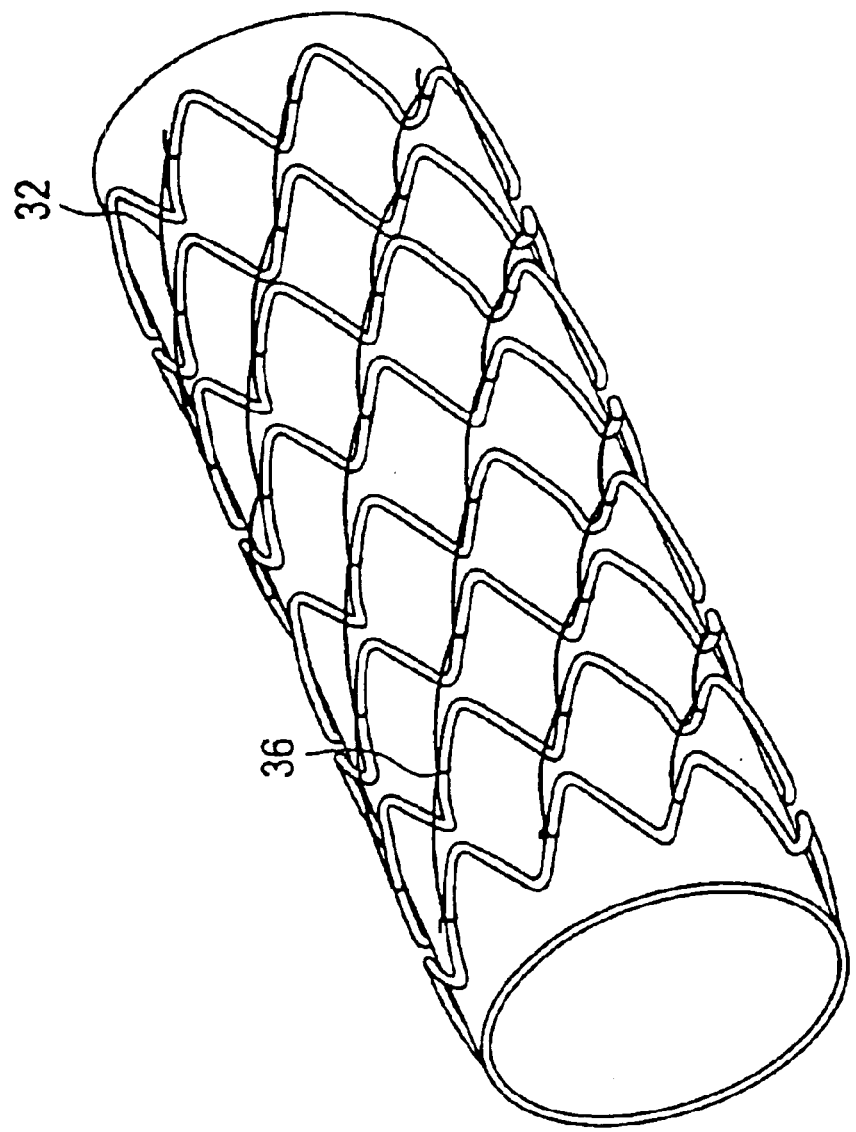
FIG. 7 is a perspective showing of yet another embodiment of an endoluminal prosthesis of the present invention wherein the securement member loops around leg segments of the stent.

FIG. 7 shows another embodiment of the present invention. Securement member consists of thin suture 32, which attaches stent 38 to tubular member 40 by forming loops 36 around leg segments 42 of stent 38. Suture 32 may be adhered to the tubular member along its length. The loops 36 are preferably adhered to the tubular member under leg segments 42 of the stent around which the loop is formed. The loops may also take the form of knots of different configurations and may be tied around the stent in many alternative methods.

Figure 8:
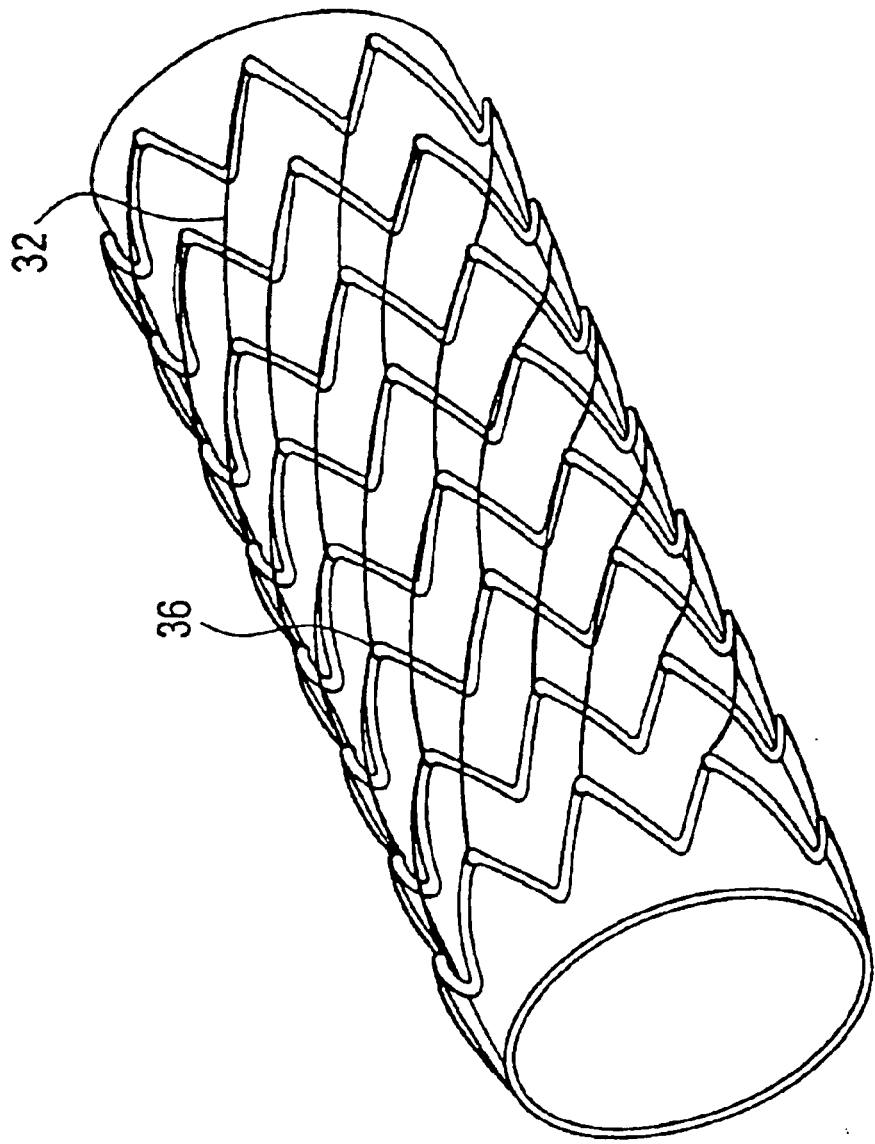
FIG. 8 is a perspective showing another embodiment of the endoluminal prosthesis of the present invention wherein a nested stent is shown with a securement member securing said stent at its elbows.

FIG. 8 shows yet another embodiment of the present invention. Stent 44 is in a nested configuration. Thin suture 32 forms loops 36 at wave-like peaks 46 in order to secure the stent to the tubular member. Similar to the prosthesis shown in FIG. 7, the loops 36 are preferably adhered to the tubular member under the stent at loop 36.

Various changes to the foregoing described and shown structures would now be evident to those skilled in the art. Accordingly, the particularly disclosed scope of the invention is set forth in the following claims.

What is claimed is:

1. An endoluminal prosthesis comprising:

an elongate tubular member having luminal surface, an exterior surface and extending along a longitudinal axis;

a structural support member disposed on the luminal or exterior surface of said tubular member; and an elongate securement member having a length and a width and securing said structural support member to said tubular member, said securement member being helically arranged at first angle with respect to said longitudinal axis and helically arranged at a second angle with respect to said longitudinal axis which intersects with said first angle to form at least one node of intersection which is adhered to itself, said width of said securement member being less than 0.60 mm.

2. The endoluminal prosthesis according to claim 1, wherein said tubular member is formed of a textile material.

3. The endoluminal prosthesis according to claim 1, wherein said elongate tubular member comprises a sheet of ePTFE wrapped to form a tube.

4. The endoluminal prosthesis according to claim 1, wherein said securement member is a substantially flat, thin suture.

5. The endoluminal prosthesis according to claim 1, wherein said securement member is formed of a textile material, said material being selected from the group consisting of PET, PTFE, and ePTFE.

6. The endoluminal prosthesis according to claim 1, wherein said securement member secures said structural support member to said exterior surface of said tubular member.

7. The endoluminal prosthesis according to claim 1, wherein said securement member is adhered to said tubular member.

8. The endoluminal prosthesis according to claim 7, wherein said securement member is non-continuously adhered to said tubular member at certain points.

9. The endoluminal prosthesis according to claim 7, wherein said securement member is continuously adhered to said tubular member, wherever said securement member interfaces with said tubular member.

* * * * *